United States Patent [19]

Brimhall et al.

[11] Patent Number: 5,151,368
[45] Date of Patent: Sep. 29, 1992

[54] DUAL AXIS, CONTINUOUS FLOW BIOREACTOR APPARATUS

[75] Inventors: Owen D. Brimhall, South Jordan; Gail A. Bowers-Irons; Joseph K. Weeks, Jr., both of Salt Lake City, all of Utah

[73] Assignee: Technical Research Associates, Inc., Salt Lake City, Utah

[21] Appl. No.: 639,966

[22] Filed: Jan. 11, 1991

[51] Int. Cl.⁵ .............................................. C12M 1/10
[52] U.S. Cl. .................................................. 435/312
[58] Field of Search ................................. 435/284–287, 435/289, 312, 313–315; 422/209; 366/287, 220, 232; 494/16–19

[56] References Cited

U.S. PATENT DOCUMENTS

| | | | |
|---|---|---|---|
| 4,114,802 | 9/1978 | Brown | 494/18 |
| 4,296,882 | 10/1981 | Kobayashi | 494/18 |
| 4,372,484 | 2/1983 | Larsson et al. | 422/101 |
| 4,425,112 | 1/1984 | Ito | 494/18 |
| 4,874,358 | 10/1989 | Brimhall et al. | 494/18 |
| 4,939,087 | 7/1990 | Van Wie et al. | 435/312 |

Primary Examiner—Robert J. Warden
Assistant Examiner—M. W. Hanley
Attorney, Agent, or Firm—J. Winslow Young

[57] ABSTRACT

A dual axis bioreactor system wherein a bioreactor vessel is mounted at its longitudinal axis to a horizontal axle with the bioreactor vessel thereby being rotatable about its longitudinal axis. The horizontal axle is rotatably mounted to a vertical shaft with the vertical shaft rotating the horizontal axle in a horizontal plane. A gear system limits the rotation of the bioreactor vessel to one rotation about its longitudinal axis for each revolution of the bioreactor vessel about the vertical shaft. A flexible, multilumen conduit is affixed to the base of the bioreactor vessel at the longitudinal axis to provide fluid communication with the bioreactor vessel. The rotation rate of the vertical shaft is carefully controlled to reduce any centrifugation effects upon the contents in the bioreactor vessel while providing mixing therein. The bioreactor system is ideally suited for continuous flow reactions and is particularly advantageous in that it eliminates moving seals, openings, or other possible sources of contamination.

14 Claims, 4 Drawing Sheets

DUAL AXIS, CONTINUOUS FLOW BIOREACTOR APPARATUS

BACKGROUND

1. Field of the Invention

This invention relates to bioreactors and, more particularly, to a bioreactor mounted on a dual axis support structure to provide an aseptic, continuous flow bioreactor which eliminates the need for seals, internal mixing devices and the like.

2. The Prior Art

Biological processes are used for numerous commercial purposes ranging from production of food items such as cheese, flavorings, beverages, artificial sweeteners and the like, to non food systems such as systems for waste treatment and digestion, and mineral recovery, to name a few. In each of these applications, as well as numerous other biological systems, there is a need for an apparatus and method that will conveniently enable an operator to monitor and control various parameters of the biological system. The parameters of interest include pH, temperature, type and rate of gas introduction into the system, and degree of agitation.

Microbial systems can be valuable for numerous commercial purposes once the proper microbial agent or mixture of microbial agents has been identified and the optimum operating conditions quantified for that particular system. The operating conditions include temperature, pH, and the type and rate of introduction of gases, if any, introduced into the system. The digestion times for the various types of ores under these different operating conditions along with the selected microbial agents specifically determined to have an affinity for the particular system under consideration can be readily determined using this system.

Various low grade ore bodies such as those containing rare metals such as gallium can be processed economically with large scale microbial systems. One processing technique, for example, involves creating a large basin several thousand square meters in area. The surface of the basin is covered with an impervious membrane such as plastic or asphalt. Fractured ore is heaped on the basin and then leached using selected microbial agents, acids, and the like. The microbial agents digest the ores releasing the metals into the solution which percolates downwardly to the basin. A drain below the basin carries the solution to the further processing system.

Clearly, such a processing strategy involves the movement of massive quantities of ore so that even though the ultimate processing strategy of using a microbial-based leach is relatively inexpensive, the material handling costs to establish the leach dump will be costly if the values recovered are less than optimum. Once the leach dump with its thousands of tons of ore has been constructed, it is extremely costly to experiment with various microbial agents to attempt to determine the optimum operating parameters for that particular ore. Accordingly, it is critical to the success of any large scale microbial processing scheme to establish the optimum operating parameters for the selected microbial agents.

The desirable course of action is to use a compact bioreactor system holding a relatively small quantity of ore, say, one or two kilograms. This system is one that can be carefully monitored under selected operating conditions and with predetermined types of microbial agents. This type of bioreactor provides accurate data that can be determined relatively inexpensively and fairly quickly from a significant number of sample runs in order to optimize the microbial reaction conditions.

Conventional bioreactor technologies are disclosed in references such as Stockton et al (U.S. Pat. No. 4,892,707); Eppstein et al (U.S. Pat. No. 4,680,267); Matsumoto et al (U.S. Pat. No. 4,552,724); Wallin (U.S. Pat. No. 2,917,372); Biller (U.S. Pat. No. 3,131,212); Kersting (U.S. Pat. No. 3,274,075). Each of these references is directed to particular parameters of the microbiological process such as pH, temperature, mixing rates, gases, nutrients, etc.

Generally, the mixing action in these devices is provided by an impeller inside the reactor vessel either singly or in combination with a gas sparging system by which the various gases are dispersed into the liquid medium. However, particularly for those bioreactor systems having a high solids content, impeller erosion and/or damage is a determining factor as to the types and amounts of solids that can be processed in the conventional bioreactor.

Another important aspect of a bioreactor system is the need to have the capability for continuous flow of nutrients and/or reactants through the reactor vessel. Various systems of the prior art have been designed to meet this requirement. However, certain biological systems are highly prone to "infection" from the presence of unwanted microorganisms so that it becomes critical that adequate steps are taken to assure that the reactor vessel is suitably protected against the inadvertent introduction of infectious microorganisms. Further, the presence of stirrers, openable covers, shaft bearings, and the like, each represent a potential for inadvertent introduction of these infectious microorganisms.

Stirring itself, becomes a critical problem particularly in systems designed to handle particulate materials such as coal, tar sand, ores, and the like. Not only is the stirrer subjected to erosion through abrasion from these particulate materials, but the abraded particles from the stirrer could interfere with the analysis or even operation of the specific biological system. Stirrers also contribute unwanted shear forces in biological systems designed around the growth of filamentous microorganisms.

Continuous flow has been achieved in certain types of centrifuge apparatus. A number of prior art references are known that teach the basic concept of a dual axis mounting system to achieve continuous flow. The devices taught by these references are primarily directed toward centrifugal fluid processing systems. One such reference is that of Kobayashi (U.S. Pat. No. 4,296,882) which discloses a centrifugal separator for fluids such as blood. The container is mounted on a rotor rotatable about a vertical axis. The container is also independently rotatable about its own horizontal axis. In view of the high rates of rotation required for centrifugation, particularly for materials such as blood, the conduit leading to the separation chamber passes through the axis of the vertical shaft.

Other centrifugal liquid processing apparatus are disclosed in the references of Lolachi (U.S. Pat. No. 4,113,173); Brown (U.S. Pat. No. 4,114,802); Larsson et al (U.S. Pat. No. 4,372,484); and Ito (U.S. Pat. No. 4,425,112). In each of these references, flow through the centrifuge head is supplied by a flexible conduit passing through the vertical axis.

Further, it is well known that the forces required to accomplish separation of blood constituents, for example, are substantial unless one is using a unique dual axis continuous flow centrifugation apparatus shown in the reference of Brimhall et al (U.S. Pat. No. 4,874,358).

In view of the foregoing, it would be a significant advancement in the art to provide a bioreactor apparatus and method having the capability to process a continuous flow of materials through the bioreactor vessel in the absence of openings, or the like, which may expose the contents of the bioreactor vessel to inadvertent contamination from other microorganisms. Another advancement in the art would be to provide a bioreactor system that is subjected to continuous stirring at all times, and, more importantly, introduce the stirring action in the absence of stirrers, impellers, and the like. Such a novel bioreactor apparatus and method is disclosed and claimed herein.

BRIEF SUMMARY AND OBJECTS OF THE INVENTION

This invention is a novel, dual axis bioreactor system having a bioreactor vessel that has the capability for continuous flow of reactants and products. The bioreactor vessel is rotatable in a horizontal plane about a vertical axis. The bioreactor vessel is also rotatable about its longitudinal axis. The rate of rotation of the bioreactor in the horizontal plane is fixed to exactly match its rate of rotation about its longitudinal axis thereby enabling a flexible conduit to be coupled to the bioreactor vessel in the absence of seals. The flexible conduit is a multilumen conduit for introducing feed and gases into the bioreactor vessel while withdrawing reaction products. Sensor wires also pass through the flexible conduit. The planetary-like path of travel by the bioreactor vessel provides the desired mixing action of its contents.

It is, therefore, a primary object of this invention to provide improvements in bioreactor systems.

It is another object of this invention to provide improvements in the method of operating a bioreactor system.

Another object of this invention is to provide a bioreactor vessel that is mounted on a dual axis support system so as to accommodate a flexible conduit connected into the bioreactor vessel in the absence of seals.

Another object of this invention is to provide a bioreactor vessel wherein mixing inside the bioreactor vessel is accomplished in the absence of a mechanical impeller inside the bioreactor vessel.

Another object of this invention is to provide a closed bioreactor system having the capability of continuous flow of reactants and products particularly in the absence of seals, and the like.

These and other objects and features of the present invention will become more readily apparent from the following description with the accompanying drawing and appended claims.

DETAILED DESCRIPTION OF THE PREFERRED EMBODIMENT

Figure 1:
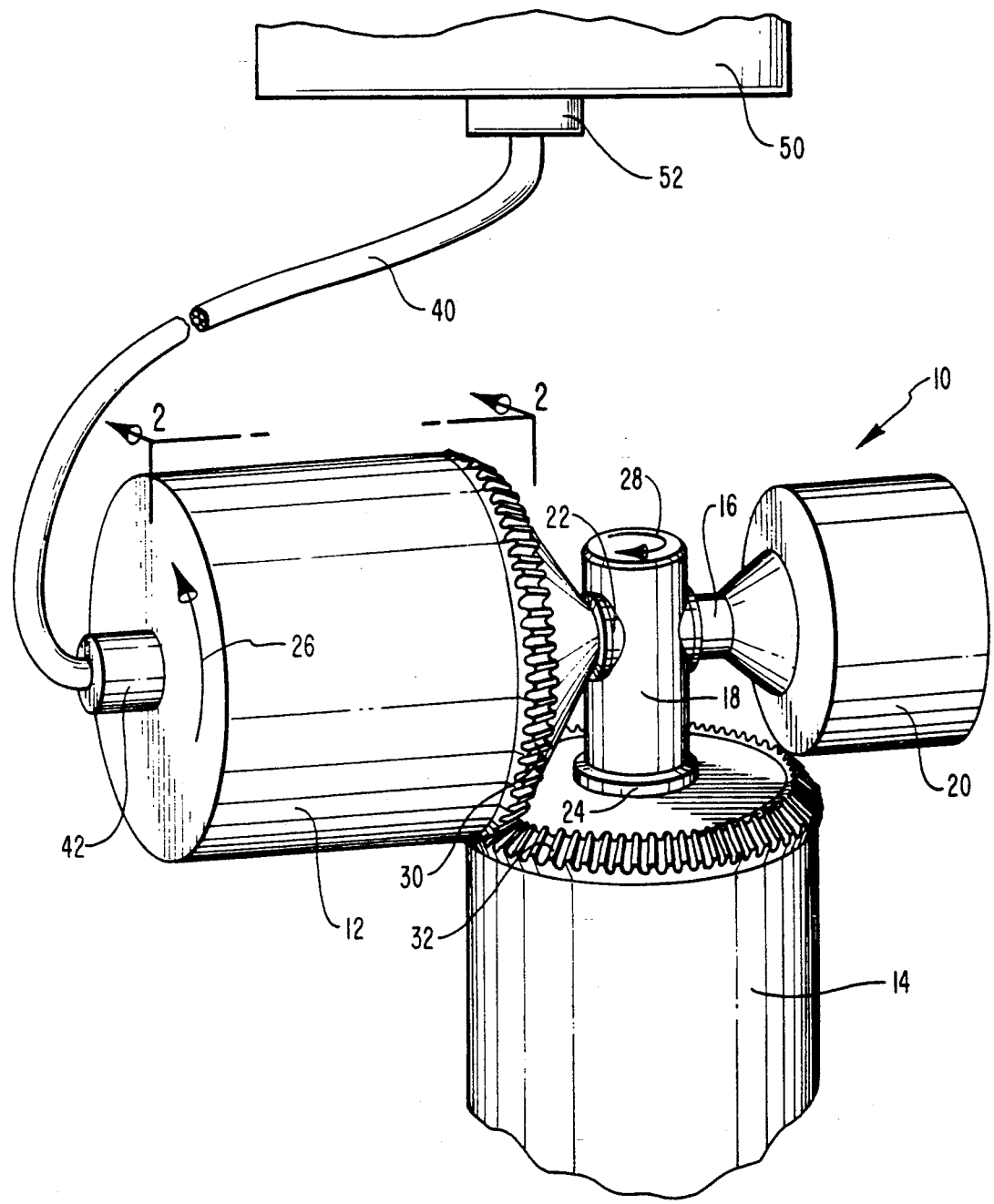
FIG. 1 is a perspective view of the novel bioreactor system of this invention.

The invention is best understood by the following description taken in conjunction with reference to the drawing wherein like parts are designated by like numerals throughout.

General Discussion

One key to progress in the biotechnology industry is the development of improved bioreactors. For example, one problem of significance in the bioprocessing of materials such as fossil energy resources as well as the bioextraction of metal values from ore is the type and amount of solids loading typically encountered with these materials. The present state of the art in bioreactor design has evolved generally from the food or pharmaceutical industries where high solids loading was not a significant factor. Commercially available laboratory bioreactors rely principally upon a relatively small number of techniques to mix and thereby provide the necessary intimate contact of fresh nutrients and gases with the microorganisms. These mixing techniques include airlift systems, turbine impellers, and vibratory or shaker systems, to name the primary systems.

The conventional handling of large volumes of solids, for example coal, requires the use of a large, horizontal, rotary vessel. Accordingly, the engineering data obtained from laboratory scale bioreactor systems is very difficult to translate into meaningful data for use in design of these large production reactors. This is due in large part to the fundamental differences in mixing technologies. For example, airlift reactors are generally unable to keep particulate solids adequately suspended in large systems. Turbine-type bioreactors are also difficult to scale. Further, the shaft seals required for turbine-type bioreactors are prone to allow contamination into the reactor vessel, a problem that is particularly acute in fermentation processes.

Impeller flooding by gas flow also lowers the efficiency of the impeller. Further, impeller speeds are often increased to maintain suspension of particulates in circumstances of high solids loading. Not only do these conditions increase mechanical wear or erosion of the impeller, but they also lead to undesirable levels of shear. An exacerbating problem in bioreactor systems is encountered with filamentous microorganisms. Additionally, all prior art techniques have difficulty in handling materials of high solids content such as tar sands, oil shales, coal, and mineral ores.

Accordingly, one key to progress in the biotechnology industry is the development of improved bioreactors, specifically an improved bioreactor oriented toward the bioprocessing of high solids loaded materials such as encountered in the processing of fossil energy resources such as coal as well as mineral ores. This novel bioreactor has the capability for mixing materials with a high solids loading as well as providing for continuous, aseptic feeding and removal of materials such as nutrients, products, gases, sampling, etc., in the absence of a rotating seal. The dual axis system of this invention means that the bioreactor vessel is rotated about its longitudinal axis one complete rotation for each revolution of the bioreactor vessel about an axis orthogonal to the longitudinal axis. Mixing inside the bioreactor vessel is accomplished by spatially varying, dynamic forces induced by the dual axis, steady state rotation, as will be discussed in greater detail hereinafter.

Advantageously, the bioreactor vessel is simple in design and has no internal fins or impellers which could give rise to localized shear damage and high wear. The special movement of the bioreactor vessel also allows for a conduit to be connected at the longitudinal axis of the bioreactor vessel thereby eliminating any requirement for a rotation seal. The availability of a non rotating seal allows the delivery of gases and nutrients along with the removal of exhaust gases and samples as well as access for various sensors without fear of contamination through the seals. To understand the importance of this latter consideration, seals in commercially available, aseptic bioreactors used in the pharmaceutical industry require static pressures above about 400 psi around the impeller shafts to maintain the integrity of the seal system for long periods.

Detailed Discussion

Figure 3:
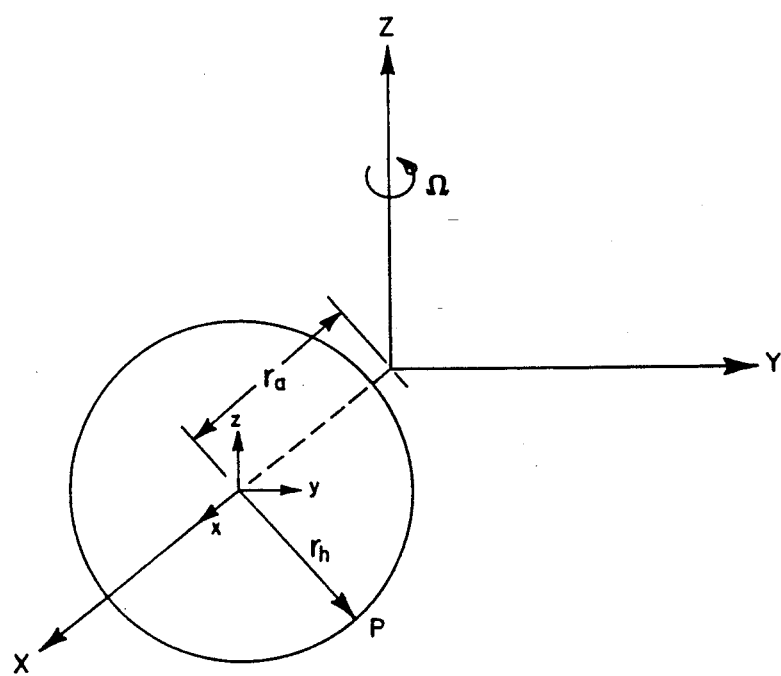
FIG. 3 is a schematic diagram for mathematically determining the mixing forces inside the bioreactor vessel.

Referring now to FIG. 3, for a discussion of the novel method of mixing in this invention, the dual axis bioreactor vessel rotates about its axis x with an angular velocity $\omega$. The center of the vessel defines a reference frame x, y, z, which rotates about the z axis with an angular velocity $\Omega$, in the x, y plane. Point P on the vessel represents the particle on which a particular force acts. A centrifugal force acting on the particle and fluid at point P is given by the buoyant mass of the particle times the absolute acceleration at that point.

Using vector notation the absolute acceleration $\vec{a}$ is given by:

$$\vec{a} = \vec{a}(x,y,z) + \vec{\Omega} \times \vec{v_h} + \vec{\Omega} \times (\vec{\Omega} \times \vec{v_h}) + 2\vec{\Omega} \times \vec{v}_{rel} + \vec{a}_{rel}$$

where
$\vec{a}(x,y,z) = \vec{\Omega} \times (\vec{\Omega} \times \vec{v_a})$, $\vec{v}_{rel} = \vec{\omega} \times \vec{v_h}$, $\vec{a}_{rel} = \vec{\omega}_x(\vec{\omega}_x \vec{v_h})$
$\vec{v_h}$ = "head" radius and $\vec{v_a}$ = "arm" radius.

For our case $\dot{\Omega} = 0$ since $\Omega$ = constant and $|\vec{\Omega}| = |\vec{\omega}|$ but must be kept separate for the vector calculation. rh and ra are the effective radii defining the position of the "particle" anywhere in a thick vessel. The absolute acceleration and hence the centrifugal force varies in a complicated though periodic way in different parts of the vessel as it swings around the z axis. For example, magnitude of the x component of the acceleration is given by $$|a_x| = -\Omega^2 v_a \cos(\Omega t) + \Omega^2 v_h \sin(\Omega t)$$
$$\sin(\omega t) + 2\Omega(\omega v_h \cos(\Omega t)\cos(\omega t)$$

The direction of the force relative to the vessel also fluctuates as the head rotates. The counter rotation of the vessel, as it rotates about the z axis, keeps the input and output tubing from twisting as the device rotates. Of course, the design also allows the connection of other conduits such as electrical connection to the vessel without twisting during the mixing process.

Referring now more particularly to FIG. 1, the novel, dual-axis bioreactor apparatus of this invention is shown generally at 10 and includes a bioreactor vessel 12 rotatably mounted on a base 14 by a horizontal axle 16 and a vertical shaft 18. A counterweight 20 is mounted to the opposite end of horizontal axle 16 and serves as a counterbalance for bioreactor vessel 12.

Horizontal axle 16 is rotatably mounted to vertical shaft 18 at a bearing 22 while vertical shaft 18 is rotatably mounted to base 14 by a bearing 24. Bioreactor vessel 12 is rotated in a counter clockwise direction about the axis of horizontal axle 16 as shown by rotation arrow 26 while being rotated in a horizontally plane about vertical shaft 18 as shown by rotation arrow 28. Importantly, the rotational relationship between bioreactor vessel 12 and base 14 is fixed such that bioreactor vessel 12 rotates one time about its axis (horizontal axle 16) as shown by rotation arrow 26 for each complete circuit of the horizontal plane about vertical shaft 18 as shown by rotation arrow 28. This fixed relationship is achieved by a matching pair of ring, bevel gears 30 and 32. Bevel gear 30 is concentric with horizontal axle 16 and is fixed to bioreactor vessel 12 while bevel gear 32 is concentric with vertical shaft 18 and is fixed to base 14.

Vertical shaft 18 is turned in bearing 24 by an electric motor (not shown) below base 14 in the direction shown by rotation arrow 28. Horizontal axle 16 is thereby moved in a horizontal plane about vertical shaft 18. The engagement of bevel gear 30 with bevel gear 32 causes bioreactor vessel 12 to turn in the direction of rotation arrow 26. Clearly, other systems may be used to assure that there is a fixed relationship between the rotation of bioreactor vessel 12 and base 14 such that bioreactor vessel 12 makes one complete rotation about its axis for each complete circuit about base 14. This feature is important since it eliminates all twisting or kinking of conduit 40.

Conduit 40 is a multilumen conduit that is flexible and of sufficient length to allow for its free movement in an arcuate path around the external periphery of the envelope defined by the path of travel of bioreactor vessel 12 in its traverse around vertical shaft 18. Conduit 40 depends downwardly from a controller 50 through a connector 52 and is coaxially connected to bioreactor vessel 12 at a vessel connector 42. Controller 50 (FIG. 5) is any suitable device for providing the various requirements to reactor vessel 12 supplied through conduit 40 as will be discussed more fully hereinafter. Importantly, conduit 40 avoids a net twisting force upon rotation of bioreactor vessel 12 about horizontal axle 16 because each traverse about the vertical shaft 18, in effect, "untwists" conduit 40 during each complete revolution of dual axis bioreactor apparatus 10.

Conduit 40 is a multilumen tubing and provides the necessary coupling of oxygen and/or other gases, exhaust ventilation, nutrients, reaction products, electrical connections, and the like, with bioreactor vessel 12. Advantageously, bioreactor vessel 12 is completely isolated against contamination, and can also be used for continuous flow reactions. Further, various types of solids/liquid streams can be processed through bioreactor vessel 12 on a continuous basis without having to open bioreactor vessel 12 or even stop its mixing action at any time.

Figure 4:
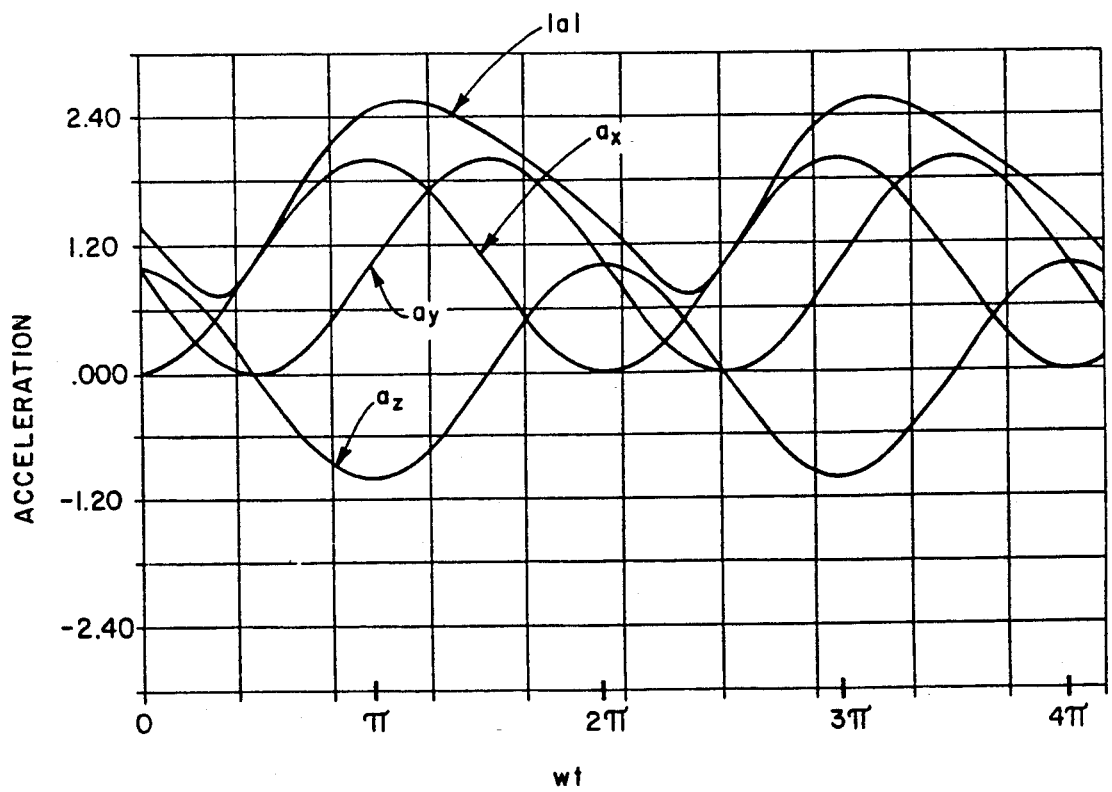
FIG. 4 is a graph illustrating the acceleration of various points inside the reactor vessel as a function of the rate of rotation.

Referring now more particularly to FIG. 4, the pulsatile nature of the mixing forces caused by the respective acceleration component is shown. Equation 4 can be solved for $a_x$, $a_y$ and $a_z$. If ra=rh=1 and $\omega = \Omega = 1$ then:

$$a_x = (1 - \cos\omega^*)$$
$$a_y = (1 - \sin\omega^*)$$
$$a_z = \cos\omega^*$$

Equation 3

The magnitude of the pulsatile acceleration (and hence the mixing force) is $$|a| = (a_x^2 + a_y^2 + a_z^2)^{\frac{1}{2}} \qquad \text{Equation 4}$$

FIG. 4 shows the nature of $a_x$, $a_y$, $a_z$ and the magnitude of a the composite force, as the point P makes two revolutions (4 pi radians).

For an ordinary, one axis, centrifuge apparatus, the acceleration component would not vary with and would equal one unit. The dual axis centrifuge or mixing acceleration component fluctuates between about 2.5 and 0.7 units.

Figure 2:
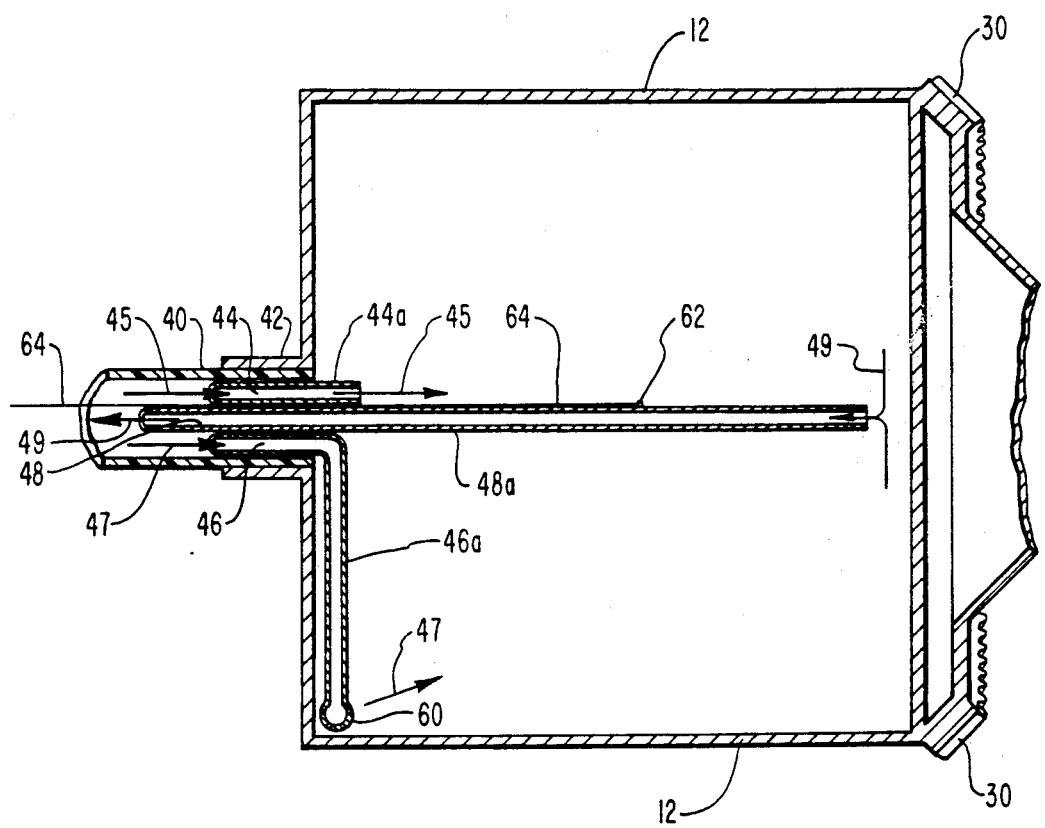
FIG. 2 is a cross sectional view of the bioreactor vessel of FIG. 1 taken along lines 2—2 of FIG. 1.

Referring now to FIG. 2, bioreactor vessel 12 is shown in cross section to reveal the internal components. In particular, conduit 40 is shown having a plurality of internal conduits or tubes 44, 46, and 48. Clearly, additional tubes may by included in conduit 40 although only three are shown herein for the purposes of this discussion. A sensor 62 on the end of a wire 64 is mounted inside bioreactor vessel 12 with wire 64 passing through conduit 40. Inside bioreactor vessel 12 each of tubes 44, 46, and 48 are connected to pipes 44a 46a and 48a, respectively. Pipes 44a, 46a, and 48a, are rigid whereas each of tubes 44, 46, and 48 are flexible as part of conduit 40, as discussed hereinbefore.

Tube 44 is designed to carry a feedstock (indicated schematically herein by arrow 45) which is introduced into bioreactor vessel 12 by pipe 44a. Feedstock 45 can be any suitable stream introduced into bioreactor vessel 12 and may include any desired mixture of liquids and-/or liquids and solids.

Tube 46 is a gas conduit for introducing gases 47 into bioreactor vessel 12. Pipe 46a is bent so as to reside adjacent a wall of bioreactor vessel 12 and terminates in a sparger 60. Gases 47 are sparged into the interior of bioreactor vessel 12 through sparger 60 which, because of its location is "beneath" the contents (not shown) of bioreactor vessel 12 due to the centrifugal forces imposed thereon during the movement of bioreactor vessel 12 described hereinbefore.

Gases generated by the reaction inside bioreactor vessel 12 as well as other reaction products are withdrawn from bioreactor vessel 12 through pipe 48a as shown schematically by flow arrows 49. Pipe 49 terminates in an opening adjacent the "upper" surface of the reactants (not shown) inside bioreactor vessel 12. The "upper" surface results from the centrifugal forces imposed on the reactants (not shown).

Figure 5:
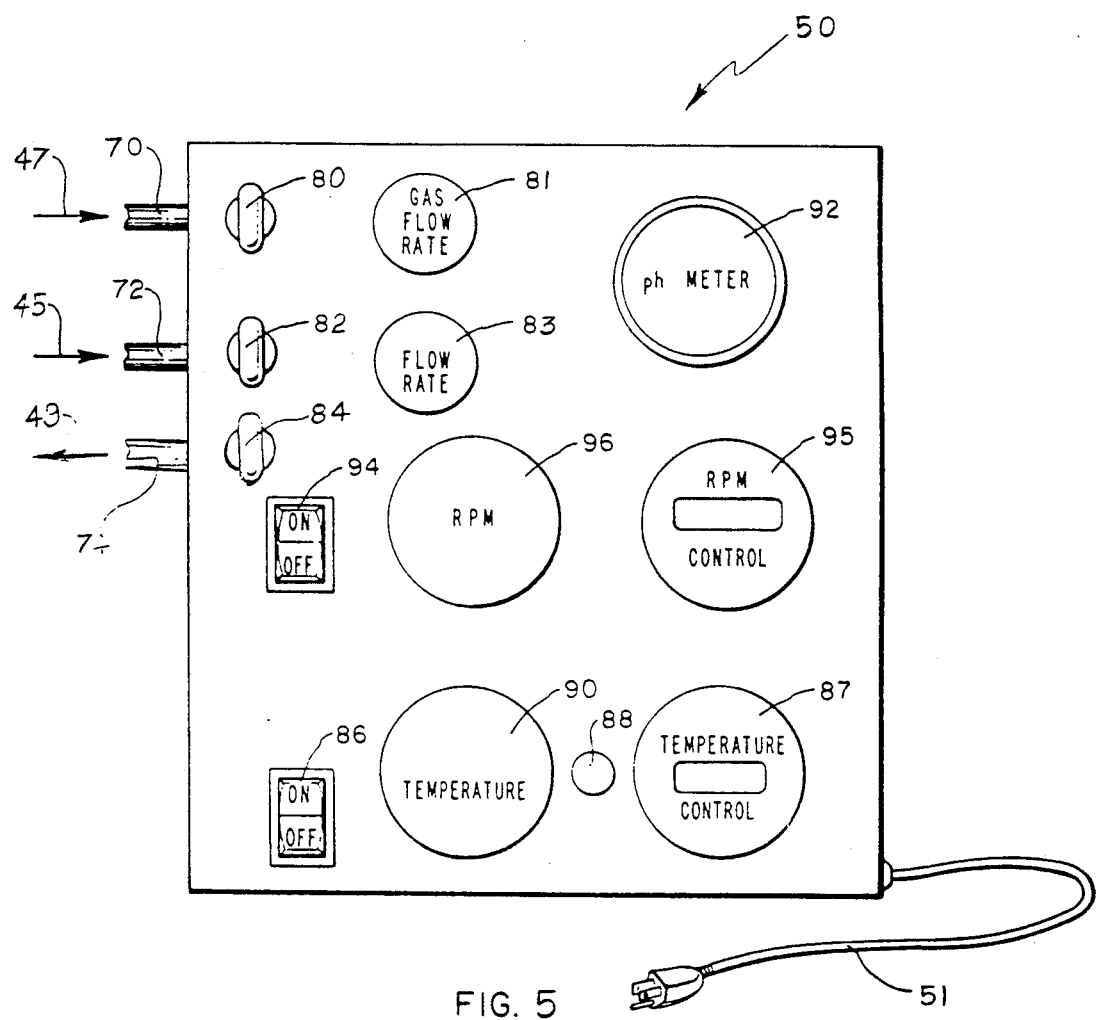
FIG. 5 is a frontal elevation of a controller for the bioreactor.

Referring now to FIG. 5, controller 50 is shown having a conventional electrical power cord 51, for supplying the necessary electrical power. Feed conduits 70 and 72 pass through controller 50 where the fluids flowing therethrough (gas 47 and feed stream 45, respectively) are regulated by valves 80 and 82, respectively. Meters 81 and 83 indicate the respective flow rates of gas 47 and feed stream 45. Clearly, other feed stream gases can be introduced into bioreactor vessel 12 (FIGS. 1 and 2) although only two are shown herein for ease of illustration. Feed stream 45 is any suitable feed stream and may include nutrients, supplemental microorganisms, reactants, and the like. Conventionally feed stream 45 includes water as the primary constituent with these other ingredients either dissolved therein or suspended in the moving water stream of feed stream 45. Gases used in bioreactor vessel 12 can be any suitable gas or mixture of gases including, for example, air, nitrogen, oxygen, carbon dioxide, etc.

Temperature control 87 is used to set the temperature within bioreactor vessel 12 (FIGS. 1 and 2) by controlling the electrical energy to a conventional resistance heater (not shown). A light 88 indicates when electrical energy is being supplied to the heater. The temperature inside bioreactor vessel 12 is sensed by a thermocouple such as sensor 62 to which a thermocouple lead or electrical conduit 64 interconnects sensor 62 with a temperature gauge 90. Alternatively, sensor 62 could also be a pH sensor that transmits a signal through electrical conduit 64 to a pH meter 92 to provide a readout of the pH inside bioreactor vessel 12.

Product stream 49 exits controller 50 through an outlet 74 regulated by a valve 84. Flow rate meter 83 can also be a dual purpose flow rate meter in that it will also indicate the flow rate of product stream 49. In this manner, controller 50 can be operated by an operator (not shown) or even by a computer (not shown) to achieve the desired control of RPM, temperature, pH, gas flow rate, feed stream flow rate, and product stream flow rate, for example.

The Method

A premeasured, analyzed, and suitably prepared reactant 45 (FIG. 2) is introduced into bioreactor vessel 12 through tubing 44 and pipe 44a by means of conduit 40 from controller 50. Reactant 45 can be selected from a wide range of materials including nutrients, microbial agents, analytes, ores, fossil fuels, and the like. Gases 47, if any, are distributed throughout bioreactor vessel 12 by the travel of sparger 60 as it completes the rotary path described by bioreactor vessel 12 in its rotation about horizontal axle 16. Byproducts and products, whether liquids or gases are withdrawn from bioreactor vessel as shown by arrow 49

Importantly, the entire bioreactor system 10, which includes bioreactor vessel 12, conduit 40, and controller 50, is a closed system thereby precluding the opportunity for contamination that would otherwise be probable if one were to use a conventional bioreactor system of the prior art. Further, bioreactor system 10 is a continuous flow system because of the unique, dual-axis mounting system employed. In particular, conduit 40 is securely coupled to bioreactor vessel 12 at a fitting 42 in the absence of any form of sliding seal. The only requirement for conduit 40 in this configuration is that it must be sufficiently flexible to accommodate the flexure encountered and of sufficient length so as to enable it to follow the circular path described by bioreactor vessel 12 in its path about vertical shaft 18.

The rotation rate for bioreactor vessel 12 is substantially less than that for centrifugation apparatus due to the fact that one of the primary reason for the dual axis mounting system for bioreactor vessel 12 is to take advantage of the mixing action resulting therefrom. At the higher speeds required for centrifugation, the mixing forces are effectively nullified by the greater centrifugal forces. In fact, during centrifugation it is highly desirable to virtually eliminate all mixing action since any mixing of the contents would severely interfere with the desired separation action to be obtained through centrifugation.

As described hereinbefore, especially with respect to FIGS. 3 and 4, the mixing action inside bioreactor vessel 12 is quite complicated to describe since it involves a combination of low centrifugal forces about the vertical shaft 18 as well as those about horizontal axle 16. Advantageously, thorough mixing is accomplished while, simultaneously, continuous flow is provided through conduit 40. All this is achieved in the absence of impellers, seals, openings, etc., that are required in the teachings of the prior art.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A dual axis bioreactor system comprising:
   a bioreactor vessel rotatably mounted on a horizontal axis with said horizontal axis being rotatably mounted to a rotatable vertical shaft so as to move said bioreactor vessel in a circular path about said vertical shaft while simultaneously rotating said bioreactor vessel about said horizontal axis;
   interlock means between said horizontal axis and said vertical shaft so as to exactly limit one rotation of said bioreactor vessel about said horizontal axis for each traverse of said bioreactor vessel through said circular path about said vertical shaft;
   conduit means for providing fluid communication with said bioreactor vessel, said conduit means comprising a flexible, multilumen conduit fixed to said bioreactor vessel at said horizontal axis of said bioreactor vessel and at a position opposite said vertical shaft; and
   control means for limiting the rate of rotation of said vertical shaft to encourage internal mixing inside said bioreactor vessel, said internal mixing occurring preferentially over any centrifugal effects on said bioreactor vessel.

2. The dual axis bioreactor system defined in claim 1 wherein said interlock means comprises a first bevel ring gear affixed to said bioreactor vessel and said vertical shaft comprises a base with a second bevel ring gear mounted to said base concentric with said vertical shaft and in engagement with said first bevel ring gear.

3. The dual axis bioreactor system defined in claim 1 wherein said multilumen conduit comprises at least one electrical conduit.

4. The dual axis bioreactor system defined in claim 3 wherein said multilumen conduit comprises a first conduit for introducing a feed stream into said bioreactor vessel, a second conduit for introducing a gas stream into said bioreactor vessel, and a third conduit for removing products from said bioreactor vessel.

5. The dual axis bioreactor system defined in claim 4 wherein said second conduit comprises a gas sparger inside said bioreactor vessel for sparging said gas stream inside said bioreactor vessel.

6. The dual axis bioreactor system defined in claim 4 wherein said third conduit comprises a discharge pipe extending inwardly into said bioreactor vessel along said horizontal axis to a point in said bioreactor vessel adjacent said vertical shaft.

7. The dual axis bioreactor system defined in claim 1 wherein said bioreactor vessel comprises a counter balance means for balancing said dual axis bioreactor system upon rotation of said bioreactor vessel about said vertical shaft.

8. A dual axis bioreactor system comprising:
   a base;
   a vertical shaft rotatably mounted to said base;
   a horizontal axle rotatably mounted to said vertical shaft;
   a bioreactor vessel mounted to said horizontal axle, said bioreactor vessel having a longitudinal axis corresponding to said horizontal axle;
   engagement means between said bioreactor vessel and said base for limiting rotation of said bioreactor vessel to exactly one rotation of said bioreactor vessel about said longitudinal axis for each rotation of said vertical shaft;
   flexible conduit means affixed to said bioreactor vessel at said longitudinal axis at a point on said bioreactor vessel opposite said vertical shaft; and
   control means for controlling the rate of rotation of said vertical shaft.

9. The dual axis bioreactor system defined in claim 8 wherein said engagement means comprises a first bevel ring gear mounted to and concentric with said horizontal axle and a second bevel ring gear mounted to said base and concentric with said vertical shaft, said first bevel ring gear being meshed with said second bevel ring gear; said first bevel ring gear being identical to said second bevel ring gear.

10. The dual axis bioreactor system defined in claim 8 wherein said multilumen conduit comprises at least one electrical conduit.

11. The dual axis bioreactor system defined in claim 10 wherein said multilumen conduit comprises a first conduit for introducing a feed stream into said bioreactor vessel, a second conduit for introducing a gas stream into said bioreactor vessel, and a third conduit for removing products from said bioreactor vessel.

12. The dual axis bioreactor system defined in claim 11 wherein said second conduit comprises a gas sparger inside said bioreactor vessel for sparging said gas stream inside said bioreactor vessel.

13. The dual axis bioreactor system defined in claim 11 wherein said third conduit comprises a discharge pipe extending inwardly into said bioreactor vessel along said horizontal axis to a point in said bioreactor vessel adjacent said vertical shaft.

14. The dual axis bioreactor system defined in claim 8 wherein said bioreactor vessel comprises a counter balance means for balancing said dual axis bioreactor system upon rotation of said bioreactor vessel about said vertical shaft.

* * * * *